Dec. 17, 1974 W. A. WARRINER Plant Pat. 3,664
ROSE PLANT
Filed Dec. 6, 1973
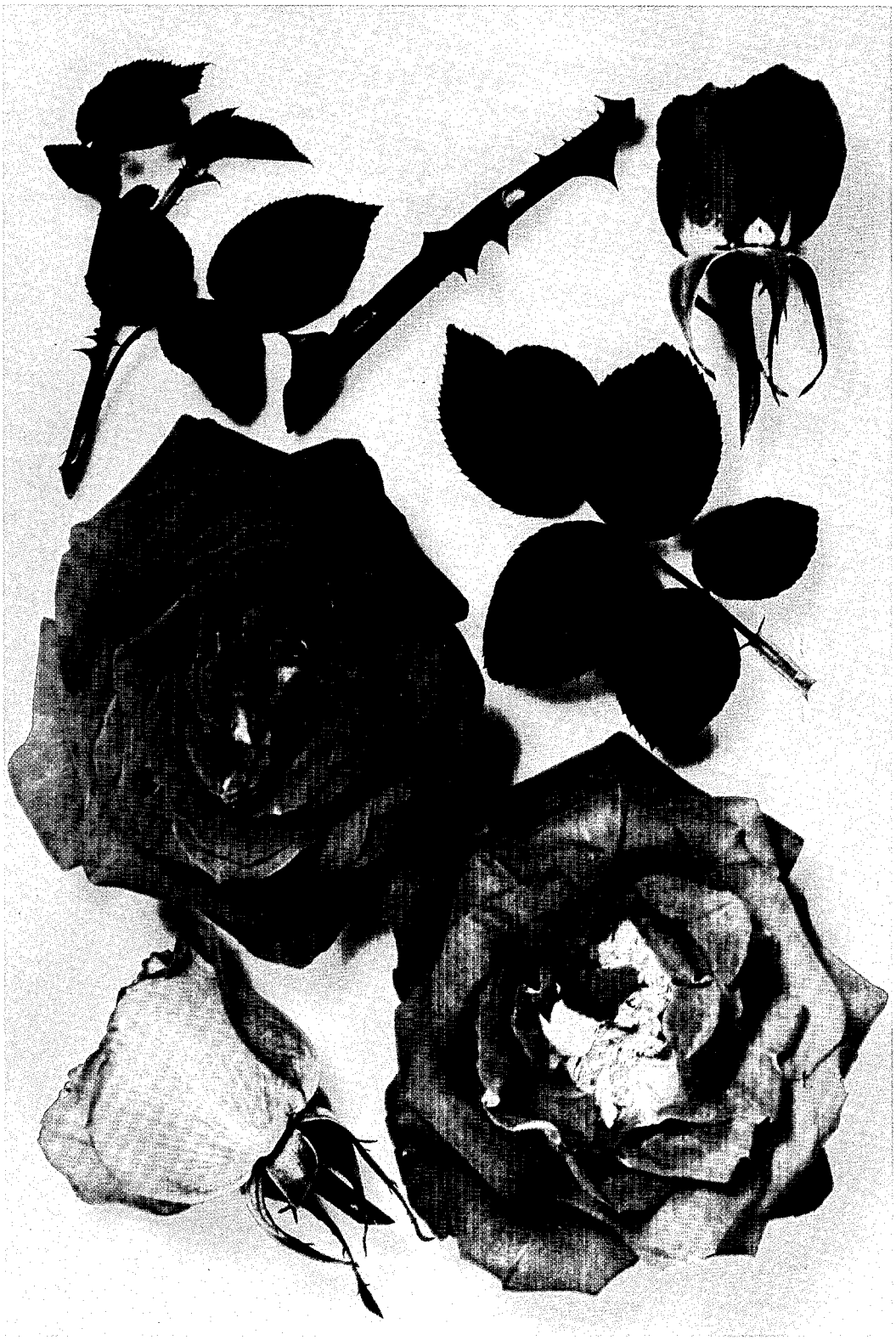

United States Patent Office

Plant Pat. 3,664
Patented Dec. 17, 1974

3,664

ROSE PLANT

William A. Warriner, Tustin, Calif., assignor to Jackson & Perkins Company, Medford, Oreg.

Filed Dec. 6, 1973, Ser. No. 422,207
Int. Cl. A01h 5/00
U.S. Cl. Plt.—21 1 Claim This present invention relates to a new and distinct cultivar of rose plant of the hybrid tea class which was originated by me by crossing the cultivar Tropicana, U.S. Pl. Pat. 1,969 with pollen from the cultivar Living, U.S. Pl. Pat. 1,463.

The primary objective of this breeding was to produce a cultivar of vigorous growth, freedom of bloom, large flowers of brilliant color. This objective was substantially achieved along with other desirable improvements as evidenced by the following unique combination of characteristics which are outstanding in the new cultivar and which distinguish it from its parents as well as from all other cultivars of which I am aware:

1. A vigorous, upright habit of growth, more upright than Tropicana and more vigorous than Living.
2. A large bud and open flower usually of 35 to 40 petals.
3. A deep red bud and flower color with a decidedly lighter color on the reverse side of the petals.
4. A distinctive and unusually prominent white veining effect, this veining is more pronounced during spring than during summer and autumn.
5. Very little fragrance.

Asexual reproduction of this new variety by budding, as performed at Wasco, Calif., shows that the foregoing characteristics and distinctions come true to form and are established and transmitted through succeeding propagations.

The accompanying drawing shows typical specimens of the vegetative growth and flowers of this new variety in different stages of development, depicted in color as nearly true as it is reasonably possible to make the same in a color illustration of this character.

The following is a detailed description of my new rose variety with color terminology in accordance with *Munsell Book of Color,* except where ordinary dictionary significance of color is indicated.

Parentage: Seedling.
*Seed parent.*—Tropicana, U.S. Pl. Pat. 1,969.
*Pollen parent.*—Living, U.S. Pl. Pat. 1,463.
Classification:
*Botanic.*—Rosa hybrid.
*Commercial.*—Hybrid tea.

FLOWER

Observations were made at Irvine, Calif. in late September.

Blooming habit: Recurrent—continuous.
Bud:
*Size.*—1¼ to 1½ inches when petals start to unfurl.
*Form.*—Pointed, ovoid, broad base.
*Color.*—When sepals first divide near Red 5.0 R 3/12 with basal area of yellow 5.0 Y 9/8 and some white veining visible. When half blown; upper side of petals near Red 5.0 R 3/2; lower side of petals near Purplish Red 2.5 R 5/12 with prominent white veining giving nearly a bicolor effect.
*Sepals.*—Color: Outer surface—Green Yellow 7.5 Gy 6/8, stippled heavily with Red 5.0 R 3/10. Inner surface—mostly near Red 5.0 R 3/10 covered with white tomentum. Three appendaged sepals lightly appendaged. Two unappendaged sepals serrated, hairy edged.

*Receptacle.*—Color: Green Yellow 7.5 Gy 6/8 with shaded areas near Red 5.0 R 3/10. Shape: Short funnel. Size: Broad. Surface: Slightly glandular.
*Peduncle.*—Length: Short. Surface: Prickly. Color: Bronzy. Strength: Stiff.
*Opening.*—Spiral type with very little curling of petals until full open.
Bloom:
*Size.*—Large. Average size when fully expanded 4½" to 5".
*Borne.*—Mostly singly.
*Stem.*—Long, strong.
*Form.*—When first open, high centered. Permanene—flattens, outer petal edges sllightly curled.
*Petalage.*—Number of petals under normal conditions, 35–40.
*Color.*—Center of flower: Upper side of petals near Red 5.0 R 3/12. Reverse side of petals—loses white veining when open to become mostly near Purplish Red 2.5 R 5/12. Outer petals: Upper side of petals same as center of flower. Reverse of petals same as center of flower. Base of petals: Sharply defined small area of near Yellow 5.0 Y 9/6. General tonality from a distance—Red 5.0 R 3/12. Variegations—as noted, also occasionally a yellow midribbed petaloid.
*Discoloration.*—By third day—only slightly lighter than Red 5.0 R 3/12.
*Fragrance.*—Very slight.
Petals:
*Texture.*—Thick.
*Surface.*—Inside—satiny. Reverse—shiny.
*Shape.*—Nearly round.
*Form.*—Tips slightly recurved.
*Arrangement.*—Loosely imbricated. Petaloids in center—few.
*Persistence.*—Drop off cleanly.
*Lastingness.*—On the plant—long. As cut flower—long.
Reproductive parts:
*Stamens, Anthers.*—Large, few. Color—yellow. Arrangement—regular around styles.
*Stamens, Filaments (threads).*—Medium. Color—light yellow.
*Pollen.*—Lemon yellow.
*Styles.*—Columnar—loosely separated, of uneven lengths.
*Stigmas.*—Color—light greenish yellow.
*Ovaries.*—All enclosed in calyx.

PLANT

Form: Bush.
Growth: Very vigorous, upright, branching.
Foliage: Number of leaflets on normal mid-stem leaves, 5.
*Size.*—Large.
*Quantity.*—Normal.
*Color.*—New foliage: Near Purplish Red 2.5 R 2/8. Old foliage: Bluish Green 7.5 G 3/4.
Leaflets:
*Shape.*—Oval.
*Texture.*—Upper side—leathery, corrugated. Underside—smooth. Ribs and Veins—ordinary, impressed.
*Edge.*—Serrated.
*Serration.*—Single, small.
*Petiole (rachis).* — Color — reddish. Underside—prickles.
*Stipules.*—Long, smooth.
*Disease Resistance.*—Average resistance to mildew under normal growing conditions at Irvine, California.

Wood:

*New Wood.*—Color—dark green.

*Bark.*—Smooth.

*Old Wood.*—Color—green overlaid with purplish red 2.5 R 2/8 areas.

*Bark.*—Smooth.

Prickles:

*Quantity.*—On main stalks from base—ordinary. On laterals from stalk—ordinary.

*Form.*—Broad base, straight.

*Color.*—When young—brown.

*Position.*—Irregular.

Small Prickles:

*Quantity.*—On main stalks—few. On laterals—few.

*Color.*—Brown.

I Claim:

1. A new and distinct cultivar of rose plant of the hybrid tea class, substantially as herein shown and described, characterized particularly as to novelty by the unique combination of its vigorous, upright plant, large deep red buds and flowers with especially prominent white veining on the reverse of the petals.

No references cited.

ROBERT E. BAGWILL, Primary Examiner